United States Patent [19]

Soo et al.

[11] Patent Number: 5,102,848
[45] Date of Patent: * Apr. 7, 1992

[54] CATALYST COMPOSITION FOR OXIDATION OF ETHYLENE TO ETHYLENE OXIDE

[75] Inventors: Hwaili Soo; Pen-Yuan Chou; Madan M. Bhasin, all of Charleston, W. Va.

[73] Assignee: Union Carbide Chemicals & Plastics Technology Corporation, Danbury, Conn.

[*] Notice: The portion of the term of this patent subsequent to Mar. 13, 2007 has been disclaimed.

[21] Appl. No.: 589,213

[22] Filed: Sep. 28, 1990

[51] Int. Cl.$^5$ .................. B01J 27/055; B01J 23/50; B01J 23/68
[52] U.S. Cl. .................................................. 502/218
[58] Field of Search ................ 502/347, 348, 217, 218

[56] References Cited

U.S. PATENT DOCUMENTS

| | | | |
|---|---|---|---|
| 2,671,764 | 3/1954 | Sacken | 502/218 |
| 4,123,385 | 10/1978 | Rebsdat et al. | 502/25 |
| 4,248,740 | 2/1981 | Mitsuhata et al. | 502/348 |
| 4,414,135 | 11/1983 | Nojiri et al. | 502/224 |
| 4,419,276 | 12/1983 | Bhasin et al. | 502/347 |
| 4,455,392 | 6/1984 | Warner et al. | 502/347 |
| 4,701,437 | 10/1987 | Boxhoorn et al. | 502/348 |
| 4,766,105 | 8/1988 | Lauritzen | 502/347 X |
| 4,783,437 | 11/1988 | Boxhoorn | 502/348 |
| 4,806,518 | 2/1989 | Boxhoorn et al. | 502/348 X |
| 4,808,738 | 2/1989 | Lauritzen | 549/536 |
| 4,820,675 | 4/1989 | Lauritzen | 502/347 X |
| 4,829,044 | 5/1989 | Boxhoorn et al. | 502/348 |
| 4,833,261 | 5/1989 | Lauritzen | 549/536 |
| 4,874,739 | 10/1989 | Boxhoorn | 502/218 |
| 4,908,343 | 3/1990 | Bhasin | 502/218 |
| 4,908,343 | 3/1990 | Bhasin | 502/218 |
| 4,916,243 | 4/1990 | Bhasin et al. | 549/534 |

OTHER PUBLICATIONS

Kirk-Othmer, Encyclopedia of Chemical Technology, 3rd ed., 1980, Wiley & Sons, Inc., vol. 10, pp. 812–817.
U.S. Ser. No. 251,814, filed Oct. 3, 1988.
British Patent Specification 590,479.

Primary Examiner—W. J. Shine
Assistant Examiner—Douglas J. McGinty
Attorney, Agent, or Firm—Jean B. Mauro

[57] ABSTRACT

Catalysts for the epoxidation of ethylene in the vapor phase comprise silver impregnated support having thereon at least one cation promoter and oxyanion promoter comprising (i) sulfate anion, (ii) fluoride anion and (iii) oxyanion of an element of Group 3b to 6b, inclusive, of the Periodic Table, wherein the amount of fluoride anion is sufficient to reduce ethylene oxide burning.

17 Claims, No Drawings

CATALYST COMPOSITION FOR OXIDATION OF ETHYLENE TO ETHYLENE OXIDE

This invention pertains to catalysts and processes for using the catalysts for the epoxidation of ethylene to produce ethylene oxide. In particular, the catalysts provided by this invention attenuate the adverse effects when the catalysts contain efficiency-enhancing oxyanion promoters that also cause ethylene oxide burning.

BACKGROUND

The presently commercially-practiced processes for the manufacture of ethylene oxide from ethylene involve the epoxidation of ethylene over a silver containing catalyst in the presence of an oxygen-containing gas and vaporous organochloride inhibitor at elevated temperature and pressures. Considerable effort has been devoted by researchers in the field to enhance the efficiency of consumed ethylene to the sought ethylene oxide product. The primary thrust of these efforts has been toward the addition of catalyst performance-enhancing promoters to the catalysts.

U.S. Pat. No. 4,908,343 and a related United States patent application Ser. No. 251,814, filed Oct. 3, 1988, disclose the use of cations containing at least cesium cation and oxyanions of an element other than oxygen therein being selected from groups 3b through 7b, inclusive, of the Periodic Table of the Elements (as published by The Chemical Rubber Company, Cleveland, Ohio, in CRC Handbook of Chemistry and Physics, 46th Edition, inside back cover, all references herein to the Periodic Table of the Elements will be to the version set forth therein). These oxyanions, while appearing to provide enhanced efficiency of conversion of ethylene to ethylene oxide, generally also promote the burning of ethylene oxide, once formed, to undesirable combustion products, particularly at the higher ethylene oxide production concentrations which are commercially atttractive. Accordingly, catalysts are sought which attenuate ethylene oxide burning in the presence of these types of oxyanions.

U.S. Pat. No. 4,908,343 discloses impregnated silver catalysts on a support in which there is provided a mixture of at least one cesium salt and one or more alkali metal and alkaline earth metal salts. The anions of the cesium salts comprise oxyanions of elements other than the oxygen therein having atomic numbers of at least 15 to 83 and being from groups 3b through 7b, inclusive, of the Periodic Table, and the salts of the alkali metals and/or alkaline earth metals comprise at least one of halide of atomic number of 9 to 53, inclusive, and oxyanions of elements other than oxygen therein having an atomic number of either (i) 7 or (ii) 15 to 83, inclusive, and selected from the groups 3a to 7a, inclusive, and 3b to 7b, inclusive, of the Periodic Table. Often the catalyst contains at least one anion other than an oxyanion of an element of groups 3b to 7b. At column 15, lines 62 et seq., the patent relates:

"The types of oxyanions suitable as counterions for the alkali and alkaline earth metals provided in the catalysts of this invention comprise by way of example only, sulfate $SO_4{}^{-2}$, phosphates e.g., $PO_4{}^{-3}$, manganates, e.g., $MnO_4{}^{-2}$, titanates, e.g., $TiO_3{}^{-2}$, tantalates, e.g., $Ta_2O_6{}^{-2}$, molybdates, e.g., $MoO_4{}^{-2}$, vanadates, e.g., $V_2O_4{}^{-2}$, chromates, e.g., $CrO_4{}^{-2}$, zirconates, e.g, $ZrO_3{}^{-2}$, polyphosphates, nitrates, chlorates, bromates, tungstates, thiosulfates, cerates, and the like. The halide ions include fluoride, chloride, bromide and iodide.

Examples 30, 33, 36, 37, 38 and 42 of U.S. Pat. No. 4,908,343 illustrate catalysts prepared on alpha-alumina carriers made using a fluorine-containing substance as a fluxing agent. These carriers contain residual fluoride anion. The catalysts contain sulfate anion and at least one oxyanion of an element of groups 3b to 7b of the Periodic Table.

U.S. Pat. No. 4,874,739 also discloses the use of a fluorine-containing substance in preparing support for ethylene oxide catalysts. Examples 1 and 2 of that patent disclose admixing stannosulfate and cesium fluoride with aluminum oxide and then calcining an extrudate of this mixture to form an alpha-alumina support for catalysts prepared from silver oxalate, cesium hydroxide, ammonium perrhenate and ammonium sulfate. U.S. Pat. No. 4,829,044 discloses in the example a support prepared by mixing cesium fluoride with alumina and then calcining the alumina. The resultant alpha-alumina is used to prepare a catalyst from silver oxalate, cesium hydroxide, ammonium perrhenate and ammonium sulfate. See also U.S. Pat. Nos. 4,701,437; 4,783,437; and 4,806,519.

British Patent Specification 590,479 discloses ethylene oxide catalysts using a silicon support. The patent indicates that the activity of the catalysts may be promoted or modified by elements or compounds which are known to promote or modify the catalytic activity of silver metal such as gold, copper, platinum, nickel, and iron; the metal oxides and other metal compounds, particularly the alkali metal and alkaline earth metal oxides, hydroxides and carbonates; and some halogen compounds. At page 4, line 73 et seq., the patent discloses that a preliminary treatment of the silicon support material with a dilute hydrofluoric acid solution usually provides a more active catalyst.

U.S. Pat. No. 4,414,135 pertains to silver-based catalysts containing bromine and/or fluorine as an anionic component for the production of ethylene oxide. The patentees state at column 1, lines 30 to 36:

"These investigations have led to the discovery that the use of the aforesaid specified halogen elements . . . previously believed to have a poisonous action, in combination with sodium and cesium unexpectedly gives a catalyst having greatly increased performance."

U.S. Pat. No. 4,123,385 discloses a silver ethylene oxide catalyst containing cesium and rubidium and states at column 2, line 61, et seq:

"It is of little importance with which radical (anion) cesium and/or rubidium is associated. They can be inorganic or organic radicals, especially in the form of salts, hydroxides, alcoholates and phenolates. However, this radical should not consist of substances which, in particular after treatment with the gaseous reaction mixture for the preparation of ethylene oxide at 230° to 270° C., act as a so-called 'catalyst poison.' Radicals (anions) suitable for the process can be, for example: sulfate, nitrite, chloride, bromide, fluoride, chlorate, bromate, cyanate, silicate, oxalate, malonate, succinate, butyrate, laurate, stearate, benzoate and phenolate."

"Formates, acetates, carbonates, bicarbonates, nitrates, hydroxides or alcoholates of aliphatic alcohols with 1 to 3 C atoms are preferably employed."

U.S. Pat. No. 4,419,276 discloses ethylene oxide catalysts containing various cation promoters, e.g., alkali metal promoters. The patent states at column 8, lines 32 et seq:

"Suitable alkali metal promoter compounds include all those soluble in particular the solvent or solubilizing agent employed. Accordingly, inorganic and organic compounds of alkali metals, such as, nitrates, halides, hydroxides, sulfates and carboxylates may be used."

A similar disclosure is found in U.S. Pat. No. 4,455,392 at column 8, lines 36 et seq., and in U.S. Pat. No. 4,916,243 at column 16, lines 48 et seq.

U.S. Pat. No. 4,808,738 discloses ethylene oxide catalysts containing silver, a promoting amount of alkali metal, a promoting amount of rhenium and a promoting amount of rhenium co-promoter selected from sulfur, molybdenum, tungsten, chromium and mixtures thereof on a porous refractory support. At column 11, lines 23 et seq., the patent speculates that these co-promoters, which are preferably anions such as sulfate, molybdate, tungstate and chromates, can be prepared by the reactive dissolution of various non-anionic materials such as the oxides as well as other materials such as halides, oxyhalides, hydroxyhalides, hydroxides, sulfides, etc., of the metals. At column 14, lines 15 et seq., the patent states:

"There are known excellent methods of applying the promoters coincidentally with the silver on the carrier. Suitable alkali metal salts are generally those which are soluble in the silver-impregnating liquid phase. Besides the above-mentioned compounds may be mentioned the nitrites; the halides, such as fluorides, chlorides, iodides, bromides; oxyhalides; bicarbonates; borates; sulfates; sulfites; bisulfates; acetates; tartrates; lactates; and isopropoxides, etc."

See also, U.S. Pat. Nos. 4,766,105; 4,820,675 and 4,833,261.

U.S. Pat. Nos. 2,671,764 and 4,248,740 disclose the presence of sulfate in silver catalysts for the epoxidation of ethylene.

SUMMARY OF THE INVENTION

By this invention catalysts and processes for using the catalysts are provided for the epoxidation of ethylene to produce ethylene oxide which benefit from the enhanced efficiencies capable of being provided by efficiency enhancing oxyanion promoters of Groups 3b to 6b, inclusive, of the Periodic Table which also have an ability to promote burning of ethylene oxide. In accordance with this invention, catalysts for the epoxidation of ethylene to ethylene oxide comprise a catalytically effective amount of silver impregnated on an inert, refractory solid support which support has an essential absence of fluoride anion, said catalyst further containing an efficiency enhancing amount, relative to the amount of silver metal, of promoter comprising cation selected from at least one member of the group of lithium, sodium, potassium, rubidium, cesium and barium and anion comprising (i) sulfate, (ii) fluoride and (iii) at least one member of the group of oxyanions of elements having atomic numbers of 21 to 74, inclusive, selected from Groups 3b to 6b, inclusive, of the Periodic Table of Elements, wherein the sulfate and fluoride anions may be in the form of fluorosulfate and the fluoride anion is also in an amount sufficient to reduce ethylene oxide burning as compared to an otherwise identical catalyst but not containing the fluoride anion and its associated cation. It is understood that the associated cation to the fluoride anion may be one or more cations although the associated cation may be referred to in the singular herein. Often, the atomic ratio of sulfur to fluorine is in the range of about 0.1:1 to 10:1, preferably about 0.3:1 to 3:1. In a preferred aspect of the invention, the cation promoter comprises cesium. In another preferred aspect of the invention the anion promoter comprises molybdate.

An aspect of this invention relates to the use of the catalysts of this invention to epoxidize ethylene in the vapor phase to ethylene oxide.

DETAILED DESCRIPTION

The catalysts of this invention are characterized by having cation promoter and a combination of anion promoters including at least one oxyanion Promoter from Groups 3b to 6b of the Periodic Table which has the ability to promote burning of ethylene oxide and sulfate anion to enhance further efficiency and fluoride anion to attenuate the ethylene oxide burning properties of the oxyanion promoter.

For purposes herein, the following definitions are used.

The term "compound" refers to the combination of a particular element with one or more different elements by surface and/or chemical bonding, such as ionic and/or covalent and/or coordinate bonding. The term "ionic" or "ion" refers to an electrically chemical charged moiety; "cationic" or "cation" being positive and "anionic" or "anion" being negative. The term "oxyanionic" or "oxyanion" refers to a negatively charged moiety containing at least one oxygen atom in combination with another element. An oxyanion is thus an oxygen-containing anion. It is understood that ions do not exist in vacuo, but are found in combination with charge-balancing counter ions.

The cation and anion promoters are provided in a promoting amount. As used herein the term "promoting amount" of a certain component of a catalyst refers to an amount of that component that works effectively to provide an improvement in one or more of the catalytic Properties of that catalyst when compared to a catalyst not containing said component. Examples of catalytic properties include, inter alia, operability (resistance to run-away), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement shows up in the activity rather than the selectivity and an operator of an ethylene oxide plant will intentionally change the operating conditions in order to take advantage of certain catalytic properties even at the expense of other catalytic properties in order to maximize profits by taking into account feedstock costs, energy costs, by-product removal costs and the like.

The promoting effect provided by the promoters can be affected by a number of variables such as for example, reaction conditions, catalyst preparative techniques, surface area and pore structure and surface chemical properties of the support, the silver and co-promoter content of the catalyst, and the presence of other cations and anions on the catalyst. The presence of other activators, stabilizers, promoters, enhancers or other catalyst improvers can also affect the promoting effects.

The STANDARD ETHYLENE OXIDE PROCESS CONDITIONS ("STANDARD CONDITIONS") for characterizing the catalysts of this invention involve the use of a standard backmixed autoclave with full gas recycle including carbon dioxide. The CONDITIONS may be operated with some variation in ethylene, oxygen and gas phase inhibitor feed. Two cases are illustrated: air process conditions, which simulates in the backmixed reactor the typical conditions employed in commercial air-type ethylene oxide processes where air is used to supply the molecular oxygen and the oxygen process conditions, which simulates in the backmixed reactor the typical conditions in commercial oxygen-type ethylene oxide processes where molecular oxygen, as such, is employed. Each case provides a different efficiency but often air as the oxygen feed, using lower concentrations of oxygen and ethylene, will yield an efficiency to ethylene oxide which is about 2 to 4 percentage points lower than that when molecular oxygen is employed as oxygen feed. The STANDARD CONDITIONS employ the well known backmixed bottom-agitated "Magnedrive" autoclaves described in FIG. 2 of the paper by J. M. Berty entitled "Reactor for Vapor Phase-Catalytic Studies", in Chemical Engineering Progress, Vol. 70, No. 5, pages 78–84, 1974. The STANDARD CONDITIONS employ 2.0 mole % ethylene oxide in the outlet gas of the reactor under the following standard inlet conditions:

| Component | Air process Conditions, Mole % | Oxygen process Conditions, Mole % |
|---|---|---|
| Oxygen | 6.0 | 8.0 |
| Ethylene | 8.0 | 30 |
| Ethane | 0.5 | 0.5 |
| Carbon Dioxide | 6.5 | 6.5 |
| Nitrogen | Balance of Gas | Balance of Gas |
| Parts per million ethyl chloride (or one-half such amount when ethylene dichloride is used) | Optimum for Efficiency | Optimum for Efficiency |

The pressure is maintained constant at 275 psig and the total outlet flow is maintained at 11.3 SCFH (Oxygen) and 22.6 SCFH (Air). SCFH refers to cubic feet per hour at standard temperature and pressure, namely, 0° C. and one atmosphere. The outlet ethylene oxide concentration is maintained at 2.0% by adjusting the reaction temperature. Thus temperature (°C.) and catalyst efficiency are obtained as the responses describing the catalyst performance.

The catalyst test procedure used in the STANDARD CONDITIONS involves the following steps:

1. 80 cc of catalyst is charged to the backmixed autoclave. The volume of catalyst is measured in a 1 inch I.D. graduated cylinder after tapping the cylinder several times to thoroughly pack the catalyst. The volume of catalyst is alternatively calculated from the packing density of the carrier and the amount of silver and additives. The weight of the catalyst is noted.

2. The backmixed autoclave is heated to about reaction temperature in a nitrogen flow of 20 SCFH with the fan operating at 1500 rpm. The nitrogen flow is then discontinued and the above-described feed stream is introduced into the reactor. The total gas outlet flow is adjusted to 22.6 SCFH for 80 c.c. of catalyst. The temperature is adjusted over the next few days so that the ethylene oxide concentration in the outlet gas is approximately 2.0%.

3. The outlet oxide concentration is monitored over the next 4–6 days to make certain that the catalyst has reached its peak steady state Performance. The temperature is periodically adjusted to achieve 2% outlet oxide. The selectivity of the catalyst to ethylene oxide and the temperature are thus obtained.

The standard deviation of a single test result reporting catalyst efficiency in accordance with the procedure described above is about 0.7% efficiency units. The standard deviation of a single test result reporting catalyst activity in accordance with the procedure described above is about 1.2° C. The standard deviation, of course, will depend upon the quality of the equipment and precision of the techniques used in conducting the rests, and thus will vary. The test results reported herein are believed to be within the standard deviation set forth above. The running of a multiplicity of tests will reduce the standard deviation by the square root of the number of tests.

Ethylene oxide burning can be ascertained by observing the rate of efficiency loss as the delta ethylene oxide production increases. The greater the rate, the more ethylene oxide burning occurs. Conveniently, catalysts can be compared under similar conditions to observe their relative ethylene oxide burning characteristics. Statistical techniques such as regression analysis are also useful. The ethylene oxide burning of the carrier itself may be ascertained by passing the effluent from an ethylene oxide reactor operating under STANDARD CONDITIONS over a bed of the carrier at substantially the same temperature and pressure as in the ethylene oxide reactor and determining the loss of ethylene oxide through burning.

The catalysts of this invention contain at least one cation promoter and anion promoter comprising a combination of (i) oxyanion of Group 3b to 6b element, (ii) sulfate and (iii) fluoride.

These promoters or modifiers are generally provided as chemical compounds. The promoters will be referred to herein in terms of cation promoters, e.g., alkali and alkaline earth metals, and anion promoters. Compounds such as alkali metal oxide or $MoO_3$, while not being ionic, may convert to ionic compounds, e.g., during catalyst preparation or in use. Whether or not such a conversion occurs, they will be referred to herein in term of cation and anion species, e.g., alkali metal or molybdate.

The catalyst preferably contains alkali metal and/or alkaline earth metal as cationic promoter. Exemplary of the alkali metal and/or alkaline earth metals are lithium, sodium, potassium, rubidium, cesium and barium. Other cationic promoters include Group 3b metal ions including lanthanide series metals. In some instances, the promoter comprises a mixture of cations, e.g., cesium and at least one other alkali metal, to obtain a synergistic efficiency enhancement as described in U.S. Pat. No. 4,916,243.

The concentration of alkali metal and alkaline earth metal salts in the finished catalyst is not narrowly critical and may vary over a wide range. The optimum cation promoter concentration for a particular catalyst will be dependent upon performance characteristics, such as, catalyst efficiency, rate of catalyst aging and reaction temperature. The concentration of cation promoter in the finished catalyst may vary from about 0.0005 to 1.0 weight percent, preferably from about 0.005 to 0.1 weight percent. Preferably, cesium salts alone, or together with at least one other alkali or alkaline earth metal salt, can be employed in the finished catalyst. The ratio is cesium salt to any other alkali metal and alkaline earth metal salt(s), if used, to achieve desired performance is not narrowly critical and may vary over a wide range. The ratio of cesium salt to the other salt(s) may vary from about 0.0001:1 to 10,000:1, preferably from about 0.001:1 to 1,000:1. Preferably, cesium comprises at least about 10, more preferably, about 20 to 100, percent (weight) of the total added alkali metal and alkaline earth metal in the finished catalyst.

The preferred amount of cation promoter deposited on or present on the surface of the carrier or catalyst generally lies between about 10 and about 4000, preferably about 15 and about 3000 and more preferably between about 20 and about 2500 ppm by weight of cation calculated on the total carrier material. Amounts between about 50 and about 2000 ppm are frequently most preferable.

In some instances, it has been found beneficial to add more anion than is required to associate with the total alkali metal and alkaline earth metal being provided to the catalyst. The reason why such additional anion is beneficial in these situations is not known. The additional anion may be added in the form of an acid, an ammonium salt, an amine salt, etc., or a portion of the alkali metal and/or alkaline earth metal may be added as an acid salt, e.g., cesium hydrogen sulfate.

The types of anion promoters or modifiers suitable for use in the catalysts of this invention comprise (i) oxyanion of Group 3b to 6b element, (ii) sulfate and (iii) fluoride anion.

The oxyanion of Group 3b to 6b of an element of the Periodic Table include those having an atomic number of 21 to 74. These oxyanions include, by way of example, titanates, e.g., $TiO_2^{-2}$; tantalates, e.g., $Ta_2O_6^{-2}$; molybdates, e.g., $MoO_4^{-2}$; vanadates, e.g., $V_2O_4^{-2}$; chromates, e.g., $Cr_2O_4^{-2}$; zirconates, e.g., $ZrO_3^{-2}$; tungstates, e.g., $WO_4^{-2}$, and cerates, e.g., $CeO_2^{-}$. The preferred oxyanions includes oxyanions of Groups 5b and 6b of the Periodic Table, especially oxyanions of vanadium, chromium, molybdenum and tungsten. The most preferred oxyanion is oxyanion of molybdenum.

The amount of oxyanion of Group 3b to 6b element is preferably sufficient to enhance efficiency of the catalyst. Often under STANDARD CONDITIONS, the amount is sufficient to provide an increase in efficiency of at least 0.5 efficiency percentage point as compared to that provided by an identical catalyst except that contains essentially none of the oxyanion of Group 3b to 6b element and any cation associated with the oxyanion is provided (such that a constant cation promoter content exists) in the form of the hydroxide or nitrate salt instead of the oxyanion salt. Generally, the amount of the 3b to 6b oxyanion promoter (calculated on the weight of the 3b to 6b element) is at least about 20 parts per million by weight (ppmw) based on the weight of the catalyst, e.g., 50 to 2000, preferably 50 to 1000, ppmw.

The catalyst also contains sulfate anion in an amount sufficient to enhance efficiency of the catalyst. The sulfate anion may be provided in various forms, e.g., sulfate, sulfite, bisulfite, bisulfate, sulfonate, persulfate, thiosulfate, dithionate, dithionite and halosulfate, e.g., fluorosulfate. The sulfates can be applied as compounds of, e.g., ammonium salts, acid or metal salts, e.g., salts of cation promoters.

Often, the amount of sulfate anion is sufficient to increase the efficiency of the catalyst under STANDARD CONDITIONS by at least about 0.5, preferably at least 1, efficiency percentage point as compared to an identical catalyst except not containing the sulfate anion but any cation being associated with the sulfate anion being provided as the hydroxide or nitrate salt such that the cation promoter is constant between the two catalysts. Frequently, the sulfate anion is provided in an amount of at least about 20, preferably between about 20 and 2000, e.g., between about 50 and 1500, ppmw based on the total weight of the catalyst. The atomic ratio of the element of the 3b to 6b oxyanion to the sulfate anion is sometimes between about 1:10 to 10:1, preferably 1:5 to 5:1.

The catalysts of this invention further contain fluoride anion in an amount sufficient to reduce ethylene oxide burning as compared to a catalyst not containing the fluoride anion. Preferably, the ethylene oxide burning is reduced by at least about 10 percent, and sometimes by at least about 50 percent. The fluoride anion may be provided as a salt or acid, e.g., hydrofluoric acid, ammonium fluoride, ammonium bifluoride, alkali metal and/or alkaline earth metal fluoride, aluminum fluoride, etc. The fluoride anion may also be provided by fluorate, fluorite, fluorosulfate, or other fluorine-containing mixed anion. The atomic ratio of sulfur anion atoms in the sulfate anion to fluorine atoms is often about 1:10 to 10:1, preferably about 1:5 to 5:1, and most preferably between about 1:3 to 3:1. The atomic ratio of the element of the 3b to 6b oxyanion to fluorine atoms is often about 1:5 to 20:1, preferably, 1:5 to 10:1.

The catalyst may contain combinations of 3b to 6b oxyanions and/or sulfate anions and/or fluoride anions as well as other anionic components, especially oxyanions of elements other than oxygen within groups 7b and 3a to 7a of the Periodic Table of the Elements such as phosphates, polyphosphates, nitrates, chlorates, bromates, borates, silicates, carbonates, manganates, permanganates, rhenates and the like, and halides such as chloride, bromide and iodide. Other salts such as sulfides may find application.

It is well recognized that many anions have complex chemistries and may exist in one or more forms, e.g., orthovanadate and metavanadate; and the various molybdate oxyanions such as $MoO_4^{-2}$, $Mo_7O_{24}^{-6}$ and $Mo_2O_7^{-2}$. The oxyanions may also include mixed metal-containing oxyanions including polyoxyanion structures. For instance, manganese and molybdenum can form a mixed metal oxyanion. Similarly, other metals, whether provided in anionic, cationic, elemental or covalent form may enter into anionic structures.

While an oxyanion, or a precursor to an oxyanion, may be used in solutions impregnating a carrier, it is possible that during the conditions of preparation of the catalyst and/or during use, the particular oxyanion or precursor initially present may be converted to another form. Indeed, the element may be converted to a cationic or covalent form. Preferably, the element is associated with oxygen, i.e., is an oxyanion, a covalent oxide or has an oxygen-containing anion. In many instances, analytical techniques may not be sufficient to precisely identify the species present. The invention is not intended to be limited by the exact species that may ultimately exist on the catalyst during use but rather reference herein to oxyanions is intended to provide guidance to understanding and practicing the invention.

Examples of anions of molybdenum, tungsten and chromium that can be suitably applied include molybdate, dimolybdate, paramolybdate, other iso- and heteropolymolybdates, etc.; tungstate, paratungstate, metatungstate, other iso- and heteropolytungstates, etc.; and chromate, dichromate, chromite, halochromate, etc. Preferred are sulfates, molybdates, tungstates and chromates.

When the catalyst comprises rhenium, the rhenium component can be provided in various forms, e.g., as the metal, as a covalent compound, as a cation or as an anion. The rhenium species that provides the enhanced efficiency and/or activity is not certain and may be the component added or that generated either during preparation of the catalyst or during use as a catalyst. Examples of rhenium compounds include the rhenium salts such as rhenium halides, the rhenium oxyhalides, the rhenates, the perrhenates, the oxides and the acids of rhenium. However, the alkali metal perrhenates, alkaline earth metal perrhenates, silver perrhenates, other perrhenates and rhenium heptoxide can also be suitably utilized. Rhenium heptoxide, $Re_2O_7$, when dissolved in water, hydrolyzes to perrhenic acid, $HReO_4$, or hydrogen perrhenate. Thus, for purposes of this specification, rhenium heptoxide can be considered to be a perrhenate, i.e., $ReO_4$. Similar chemistries can be exhibited by other metals such as molybdenum and tungsten.

Another class of promoters includes manganese components. In many instances, manganese components can enhance the activity and/or stability of catalysts. The manganese species that provides the enhanced activity and/or stability is not certain and may be the component added or that generated either during catalyst preparation or during use as a catalyst. Manganese components include, but are not limited to, manganese acetate, manganese ammonium sulfate, manganese citrate, manganese dithionate, manganese oxalate, manganous nitrate, manganous sulfate, and manganate anion, e.g., permanganate anion, manganate anion, and the like.

The total amount of anion promoter may vary widely, e.g., from about 0.0005 to 2 weight percent, preferably from about 0.001 to 0.5 weight percent based on the total weight of the catalyst. When used, the rhenium component is often provided in an amount of at least about 1, say, at least about 5, e.g., about 10 to 2000, often between 20 and 1000, ppmw calculated as the weight of rhenium based on the total weight of the catalyst.

The catalyst may also comprise scandium, a Group 3b element. The form of the scandium component in the catalyst is not certain. Scandium can be in a chemical form which is very deleterious to catalyst activity. While not wishing to be limited to theory, it is believed that scandium component having promoter activity is one or more compounds of scandium in which scandium is covalently bonded, e.g., as scandium oxide, or a cation as present in halide, sulfate, phosphate, etc., salt.

The scandium species that provides enhanced activity and/or efficiency may be the component added or that generated either during catalyst preparation or during use as a catalyst. The scandium component may be provided with the carrier or later provided on the catalyst. Scandium components that may find use in preparing the catalyst include, but are not limited to, scandium acetate, scandium ammonium sulfate, scandium citrate, scandium dithionate, scandium oxalate, scandium nitrate, scandium sulfate, scandium beta-diketone complexes (e.g., scandium acetylacetonate), scandium chloride, scandium bromide and scandium fluoride.

The optimal amount of the scandium component may vary with silver content and particle size, the amounts and types of other promoters present and the chemical and physical properties of the carrier. However, the scandium component is often present in an amount of at least 10 ppmw (parts per million by weight) calculated as the weight of scandium as the metal. If too much scandium component is used, the catalyst performance, e.g., efficiency and/or activity, may suffer. Usually, the amount of scandium component falls within the range of about 30 to 2000, preferably, 100 to 1000, ppmw calculated as the weight of scandium as the metal.

As with any catalyst for making ethylene oxide which provides optimum performance, a correlation exists among many factors. Factors frequently considered include:
 (i) the nature of the support;
 (ii) the amount of silver on or in the support;
 (iii) the components and amounts thereof in or on the support;
 (iv) the impurities or contaminants provided with the silver or other components;
 (v) the procedure to make the catalyst; and
 (vi) the conditions under which the catalyst is used to produce ethylene oxide.

The catalyst contains a catalystically-active amount of silver. The concentration of silver in the finished catalyst may vary from about 2 to 45 or more, often about 2 to 40 or more, weight percent, a commercially preferred range being from about 6% to about 35% by weight of silver. However, the optimum silver concentration for any particular catalyst will be dependent upon economic factors as well as performance characteristics, such as catalyst efficiency, rate of catalyst aging and reaction temperature.

When a high surface area, high porosity carrier is used, higher silver concentrations such as disclosed in United States patent applications Ser. Nos. 423,197, filed Oct. 18, 1989, and 556,828, filed July 23, 1990 (both herein incorporated by reference), are preferred. These catalysts are characterized by containing silver in an amount of greater than about 0.4 grams of silver per cubic centimeter of finished catalyst, which silver is supported on a carrier having a specific surface area of greater than about 0.7 $m^2/g$ and a pore volume of at least about 0.5 cc/g. The carriers have a water pore volume as measured by conventional water absorption techniques of at least about 0.5 cc/g, generally in the range of from about 0.5 to about 2.0 cc/g, preferably greater than about 0.55 cc/g, and most preferably from about 0.6 to about 0.8 cc/g.

In conjunction with such high silver concentration, the carriers of the catalysts of the present invention have a high surface area and a high pore volume. Generally, suitable carriers have a specific surface area as measured by the B.E.T. method (herein defined) of greater than about 0.7 m²/g, generally in the range of from about 0.7 m²/g to about 10 m²/g. Preferably, the specific surface area of the carrier as measured by the B.E.T. method is preferably in the range of from about 0.8 to about 1.6 m²/g, or more. The B.E.T. method for determining specific surface area is described in detail in Brunauer, S., Emmet, P. and Teller, E. *J. Am. Chem. Soc.*, 60, 309–16 (1938). Preferably, these carriers also have a water pore volume as measured by conventional water absorption techniques of greater than about 0.55 cc/g, and most preferably from about 0 6 to about 0.8 cc/g.

The support or carrier employed in the catalysts of this invention may be selected from the large number of porous refractory catalyst carriers or support materials which are considered relatively inert in the presence of the epoxidation feeds, products and reaction conditions. The preferred carriers are characterized as having an essential absence of fluoride anion, e.g., less than about 10 ppmw. Carriers may be composed, for example, of alpha-alumina, silicon carbide, silicon dioxide, zirconia, magnesia and various clays. The preferred carriers are alpha-alumina particles often bonded together by a bonding agent and have a very high purity, i.e., at least 98 wt. % alpha-alumina, any remaining components being other phases of alumina, silica, alkali metal oxides (e.g., sodium oxide) and trace amounts of other metal-containing and/or non-metal-containing additives or impurities. A wide variety of such carriers are commercially available. Alumina carriers are manufactured by United Catalysts, Inc., Louisville, Kentucky, and the Norton Company, Akron, Ohio.

In the case of alpha alumina-containing supports, preference is given to those having a specific surface area as measured by the B.E.T. method of from about 0.03 m²/g to about 10 m²/g, preferably from about 0.05 to about 5, more preferably from about 0.1 to about 3 m²/g, and a water pore volume as measured by conventional water absorption techniques of from about 0.1 to about 0.85 cc/g by volume.

Certain types of alpha alumina-containing supports are particularly preferred. These alpha alumina supports have relatively uniform pore diameters and are more fully characterized by having (1) B.E.T. specific surface areas of from about 0.1 m²/g to about 3.0 m²/g, preferably about 0.1 m²/g to about 2.0 m²/g and (2) water pore volumes of from about 0.10 cc/g to about 0.85 cc/g, preferably from about 0.25 cc/g to about 0.75 cc/g. Median pore diameters for the above-described carriers range being from about 0.5 to 50 microns. The carriers may have monomodal, bimodal or multimodal pore distributions. The surface acidity of the carrier, as determined by irreversible ammonia sorption at 100° C., is often less than about 2, preferably less than about 1.5, and often between about 0.05 to 1.0, micromoles per gram of carrier.

Carrier manufacture is typically maintained as a trade secret by carrier manufacturers. However, insights into processes for making carriers and affecting the distribution of pore sizes in carriers are provided by, for instance, Trimm, et al., "The control of Pore Size in Alumina Catalyst Supports A Review", *Appl. Catalyst.*, Vol. 21, 215 (1986); Young, et al., U.S. Pat. No. 4,575,494; Belon, et al., U.S. Pat. No. 3,172,866; Lin, et al. U.S. Pat. No. 4,356,113; Tamm, U.S. Pat. No. 4,082,697; Pearson, et al., U.S. Pat. No. 4,001,144; Carithers, U.S. Pat. No. 3,856,708; Kiovsky, et al., U.S. Pat. No. 3,850,849 and Robayashi et al., U.S. Pat. No. 3,526,602, all herein incorporated by reference.

Regardless of the character of the support or carrier used, it is preferably shaped into particles, chunks, pieces, pellets, rings, spheres, wagon wheels, cross-partitioned hollow cylinders, and the like of a size suitable for employment in fixed bed reactors.

A variety of procedures may be employed for preparing catalysts in accordance with the present invention. It is desirable that the silver and the at least one or more promoters be relatively uniformly dispersed on the catalyst. The preferred procedure comprises: (1) impregnating a porous catalyst carrier with a solution comprising a solvent or solubilizing agent, silver complex and the aforementioned anion and/or cation promoters upon the carrier, and (2) thereafter treating the impregnated support to convert the silver salt to silver metal and effect deposition of silver and the anion and cation promoters onto the exterior and interior surfaces of the support. For sake of repeatability, in the use and reuse of impregnating solutions the carrier should preferably not contain undue amounts of ions which are soluble in the impregnating solution and/or exchangeable with the promoter supplied to the catalyst, either in the preparation or use of the catalyst, so as to upset the amount of promoter which provides the desired catalyst enhancement. If the carrier contains such ions, the ions should generally be removed by standard chemical techniques such as leaching. Silver and promoter depositions are generally accomplished by heating the carrier at elevated temperatures to evaporate the liquid within the support and effect deposition of the silver and promoters onto the interior and exterior carrier surfaces. Impregnation of the carrier is the preferred technique for silver deposition because it utilizes silver more efficiently than coating procedures, the latter being generally unable to effect substantial silver deposition onto the interior surface of the carrier. In addition, coated catalysts are more susceptible to silver loss by mechanical abrasion.

The silver solution used to impregnate the carrier is comprised of a silver compound in a solvent or complexing/solubilizing agent such as the silver solutions disclosed in the art. The particular silver compound employed may be chosen, for example, from among silver complexes, nitrate, silver oxide or silver carboxylates, such as silver acetate, oxalate, citrate, phthalate, lactate, propionate, butyrate and higher fatty acid salts. Desirably, silver oxide complexed with amines is the preferred form of silver in the practice of the invention.

A wide variety of solvents or complexing/solubilizing agents may be employed to solubilize silver to the desired concentration in the impregnating medium. Among those disclosed in the art as being suitable for this purpose are lactic acid (U.S. Pat. Nos. 2,477,436 to Aries, and 3,501,417 to DeMaio); ammonia (U.S. Pat. No. 2,463,228 to West, et al.); alcohols, such as ethylene glycol (U.S. Pat. Nos. 2,825,701 to Endler, et al., and 3,563,914 to Wattimina); and amines and aqueous mixtures of amines (U.S. Pat. Nos. 2,459,896 to Schwarz; 3,563,914 to Wattimina; 3,215,750 to Benisi; 3,702,259 to Nielsen; and 4,097,414, 4,374,260 and 4,321,206 to Cavitt).

Generally, the maximum amount of silver compound that can be dissolved in the silver solution is substantially less than that ultimately required in the finished catalysts of the present invention. For example, $Ag_2O$ can be dissolved in a solution of oxalic acid and ethylenediamine to an extent of approximately 30% by weight. Vacuum impregnation of such a solution onto an alpha-alumina support of approximately 0.7 cc/g porosity results in a catalyst containing approximately 25% by weight of silver based on the entire weight of the catalyst. Accordingly, in order to obtain catalysts having a silver loading of greater than about 25 or 30%, and more, it is necessary to subject the carrier to at least two or more sequential impregnations of silver, with or without promoters, until the desired amount of silver is deposited on the carrier. In a preferred embodiment of the present invention, the concentration of the silver salt is higher in the latter impregnation solutions than in the first. For example, if a total silver concentration of say about 30% were desired in the catalyst, a low amount of silver of about 10% by weight would be deposited on the carrier as a result of the first impregnation followed by a second silver impregnation depositing the remaining 20% by weight. This low - high sequence of silver impregnation has been found to be more desirable than impregnating the carrier with about 15% silver by each of the impregnation solutions, particularly when utilizing molybdate promoted catalysts. Each of the impregnations may be followed by roasting or other procedure to render the silver insoluble.

The sequence of impregnating or depositing the surfaces of the carrier with silver and promoters is optional. Thus, impregnation and deposition of silver and salts may be effected coincidentally or sequentially, i.e., the promoters may be deposited prior to, during, or subsequent to silver addition to the carrier. The promoters may be deposited together or sequentially. For example, one or more of the salts may be deposited first followed by the coincidental or sequential deposition of silver and additional or other salts. In some embodiments of this invention, the fluoride anion may be deposited on the carrier prior to deposition of silver and other promoters, yet the beneficial reduction of ethylene oxide burning can still be achieved. When using promoters which may be adversely affected by the silver component in the impregnation solution or which may adversely effect the silver component in the impregnation solution, a sequential deposition method by which the silver is first deposited and roasted on the carrier and then the promoters are deposited on the catalyst, may be advantageously used.

Impregnation of the catalyst carrier is effected using one or more solutions containing silver and promoters in accordance with well-known procedures for coincidental or sequential depositions. For coincidental deposition, following impregnation the impregnated carrier is heat or chemically treated to reduce the silver compound to silver metal and deposit the salts onto the catalyst surfaces.

For sequential deposition, the carrier is initially impregnated with silver or promoter (depending upon the sequence employed) and then heat or chemically treated as described above. This is followed by a second impregnation step and a corresponding heat or chemical treatment to produce the finished catalyst containing silver and promoters. When promoters may adversely interfere with the deposition of silver or the components in the silver impregnation solution may interfere with the deposition of promoter, sequential depositions are preferred. The promoters may advantageously be deposited after the deposition of the silver.

In making the catalysts of this invention, some promoters such as some alkali and alkaline earth metal salts have such high melting temperatures that when deposited on the support with silver compound, and subjected to heating to convert the silver compound to silver metal, the salts may remain essentially unchanged. Of course, it is realized that alkali metal and alkaline earth metal salts having an unstable anion oxidation state will change to a stable oxidation state or states, e.g., sulfites to sulfates. When, for instance, the alkali metal or alkaline earth metal is deposited as the hydroxide or carbonate, it may be transformed in the presence of amines, which may be used in the impregnation of the catalyst, to a different salt form (i.e., nitrate) during the heating (roasting) step depending on the roast conditions.

Following each impregnation, if more than one, of the catalyst carrier, the impregnated carrier particles are separated from any remaining non-absorbed solution. This is conveniently accomplished by draining the excess impregnating medium or, alternatively, by using separation techniques, such as filtration or centrifugation. If desired, the impregnated carrier or catalyst may be washed, e.g., with water, mild acid solution or other solvent. The impregnated carrier is then generally heat treated (e.g., roasted) to effect decomposition and reduction of the silver metal compound (complexes in most cases) to metallic silver and the deposition of alkali metal and alkaline earth metal salts. Such roasting may be carried out at a temperature of from about 100° C. to 900° C., preferably from 200° to 700° C., for a period of time sufficient to convert substantially all of the silver salt to silver metal. In general, the higher the temperature, the shorter the required reduction period. For example, at a temperature of from about 400° C. to 900° C., reduction may be accomplished in about 1 to 5 minutes. Although a wide range of heating periods have been suggested in the art to thermally treat the impregnated support, (e.g., U.S. Pat. No. 3,563,914 suggests heating for less than 300 seconds to dry, but not roast to reduce, the catalyst; U.S. Pat. No. 3,702,259 discloses heating from 2 to 8 hours at a temperature of from 100° C. to 375° C. to reduce the silver salt in the catalyst; and U.S. Pat. 3,962,136 suggests ½ to 8 hours for the same temperature range), it is only important that the reduction time be correlated with temperature such that substantially complete reduction of the silver salt to metal is accomplished. A continuous or step-wise heating program is desirably used for this purpose. Continuous roasting of the catalyst for a short period of time, such as for not longer than ½ hour is preferred and can be effectively done in making the catalysts of this invention.

Heat treatment is preferably carried out in air, but a nitrogen or carbon dioxide atmosphere may also be employed. The equipment used for such heat treatment may use a static or flowing atmosphere of such gases to effect reduction, but a flowing atmosphere is much preferred.

In yet another preferred embodiment of the present invention, after impregnation of the carrier with silver solution and before any roasting step, the impregnated carrier is rinsed with a silver compound solubilizing agent. This rinsing step helps remove excess silver that is present on the surface of the support thereby helping to avoid occlusion and/or agglomeration that may have been caused by such removed excess silver. This helps to maintain the porosity of the carrier and prevent its pores from becoming plugged with agglomerated silver particles. Conditions for such a rinsing step should be mild enough such that essentially only the excess surface silver is removed. Generally, a solvent is contacted with the impregnated support, without mixing, for up to about one minute, and then drained.

A consideration in making the catalyst of this invention is to avoid the use of strongly acidic or basic solutions which can attack the support and deposit impurities which can adversely affect the performance of the catalyst. The preferred impregnation procedure of U.S. Pat. No. 4,916,243 coupled with the high roasting temperature, short residence time procedure which the patent also described is especially beneficial in minimizing such catalyst contamination. However, the use of promoter salts coupled with the high purity supports allows one to use lower temperatures though short residence times are preferred.

The particle size of silver metal deposited upon the carrier is asserted by a portion of the prior art to be a function of the catalyst preparation procedure employed. This may seem to be the case because of the limited ability of the art to effectively view the surface of the catalyst. Thus the space between the silver particles seen on the carrier has not been characterized sufficiently to say whether only such particles of silver represent the silver on the carrier. However, the particular choice of solvent and/or complexing agent, silver compound, heat treatment conditions and catalyst carrier may affect, to varying degrees, the range of the size of the resulting silver particles seen on the carrier. For carriers of general interest for the production of ethylene oxide, a distribution of silver particle sizes in the range of 0.005 to 2.0 microns is typically obtained.

The silver catalysts of the invention are particularly suitable for use in the production of ethylene oxide by the vapor phase oxidation of ethylene with molecular oxygen. The reaction conditions for carrying out the oxidation reaction are well-known and extensively described in the prior art. This applies to reaction conditions, such as temperature, pressure, residence time, concentration of reactants, gas phase diluents (e.g., nitrogen, methane and $CO_2$), gas phase inhibitors (e.g., ethylene chloride and ethylene dichloride), and the like.

Generally, the commercially-practiced processes are carried out by continuously introducing a feed stream containing ethylene and oxygen to a catalyst-containing reactor at a temperature of from about 200° C. to 300° C., and a pressure which may vary from about five atmospheres to about 30 atmospheres depending upon the mass velocity and productivity desired. Residence times in large-scale reactors are generally on the order of about 0.1-5 seconds. Oxygen may be supplied to the reaction in an oxygen-containing stream, such as air or as commercial oxygen. The resulting ethylene oxide is separated and recovered from the reaction products using conventional methods.

In commercial processes, typical operating conditions can vary and the amounts of the ingredients employed can be adjusted to achieve the best efficiencies. In particular the amounts of ethane, carbon dioxide and organic chloride can be varied to optimize efficiency for the manufacture of ethylene oxide. Ethane is an impurity contained in varying amounts in ethylene raw material. Ethane can also be added to a commercial reactor to provide better control of the chloride's inhibitor action. Typically, the amount of ethane used in commercial processes can vary from about 0.001 to about 5 mole percent for achieving optimization under both air process conditions and oxygen process conditions. As the concentration of ethane increases in the reactor, the effective surface chloride concentration on the catalyst is believed to be decreased thereby decreasing the ability of chloride to promote/inhibit reactions that increase efficiency for the manufacture of ethylene oxide. The amount of chloride, e.g., ethyl chloride or ethylene dichloride, can be varied to provide the needed promoter/inhibitor action commensurate with the ethane levels encountered in a particular process and the type of promoters or modifiers used in the catalyst. The amount of organic chloride used in commercial processes can typically vary from about 0.1 ppm to about 100 ppm for achieving optimization under both air process conditions and oxygen process conditions.

Carbon dioxide is generally considered an inhibitor, and the inhibiting effect of carbon dioxide on process efficiency may be variable with its concentration. With different types of promoters or modifiers used in preparation of the catalysts of this invention, different concentrations of carbon dioxide may be more desirable in certain commercial processes. Typically, the amount of carbon dioxide used in commercial processes can vary from about 2 to about 15 mole percent for achieving optimization under both air process conditions and oxygen process conditions. The amount of carbon dioxide is dependent on the size and type of carbon dioxide scrubbing system employed. The optimization of the amounts of ethane, carbon dioxide and organic chloride provides catalysts which are especially suitable for obtaining desired efficiencies in commercial ethylene oxide manufacture.

EXAMPLES

The following detailed procedures are provided as illustrative of methods and carriers which are useful for preparing catalysts according to the invention. These examples are by way of illustration only and are not to be construed as limiting the scope of the invention described herein.

The carrier, as indicated, is impregnated under vacuum as hereinafter described with a solution of silver complex and alkali metal and/or alkaline earth metal salts. The alkali metal and/or alkaline earth metal-containing components need not be introduced as the salts. For instance, cesium hydroxide may be used in conjunction with an ammonium salt (e.g., ammonium sulfate) or acid (e.g., sulfuric acid) or organic compound (e.g., ethylsulfonate) and under conditions of catalyst preparation or use, conversion is made to the desired species. The impregnating solutions are prepared at concentrations such that the finished catalyst contained the desired amounts of silver and promoter or modifier. The required concentration of silver and promoter in solution for the given carrier is calculated from the packing density (grams/cc) and water pore volume of the carrier which are either known or readily determined. The relationship can vary depending upon the nature of the carrier, e.g., pore volume may influence the amount of silver deposited from a given solution. The required concentration of promoter in solution is obtained by dividing the solution silver concentration by the ratio of silver to promoter desired in the finished catalyst. As noted earlier, due to the high amount of silver required in the catalysts of the present invention, at least two or more impregnations are generally required.

In preparing the catalysts, generally a desired amount of ethylenediamine (high purity grade) is mixed with indicated amounts of distilled water. Then oxalic acid dihydrate (reagent grade) is then added slowly to the solution at ambient temperature (23° C.) while continuously stirring. During this addition of oxalic acid, the solution temperature typically rises to about 40° C. due to the reaction exotherm. Silver oxide powder is then added to the diamine-oxalic acid salt-water solution while maintaining the solution temperature below about 40° C. Finally, monoethanolamine, aqueous alkali metal salt solution(s) and distilled water are added to complete the solution. The specific gravity of the resulting solution is often about 1.3–1.4 g/ml.

Carrier can be impregnated in a vessel equipped with a suitable stopcock for draining the carrier after impregnation, however, other suitable flask sizes and types can be used. A suitable size separatory funnel for containing the impregnating solution is attached to the top of the impregnating vessel, which vessel is equipped with a vacuum line. The impregnating vessel containing the carrier is evacuated to approximately 1 to 2 inches of mercury pressure for about 20 minutes after which the impregnating solution is slowly added to the carrier by opening the stopcock between the separatory funnel and the impregnating vessel until the carrier is completely immersed in solution, the pressure within the vessel being maintained at approximately 2 inches of mercury. Following addition of the solution, the vessel is opened to the atmosphere to attain atmospheric pressure. The carrier then remains immersed in the impregnating solution at ambient conditions for about 1 hour, and thereafter is drained of excess solution for about 30 minutes. The impregnated carrier is then heat treated as follows (unless stated otherwise) to effect reduction of silver salt and deposition of promoter on the surface. The impregnated carrier is spread out in a single layer on a 2⅜ inches wide endless stainless steel belt (spiral weave) and transported through a 2 inches by 2 inches square heating zone for 2.5 minutes, the heating zone being maintained at 500° C. by passing hot air upward through the belt and about the catalyst particles at the rate of 266 SCFH. The hot air is generated by passing it through a 5 ft. long by 2 inches I.D. stainless steel pipe which was externally heated by an electric furnace (Lindberg(TM) tubular furnace: 2½ inches I.D., 3 feet long heating zone) capable of delivering 5400 watts. The heated air in the pipe is discharged from a square 2 inches by 2 inches discharge port located immediately beneath the moving belt carrying the catalyst carrier. After being roasted in the heating zone, the finished catalyst is weighed, and based upon the weight gain of the carrier, and the known ratios of silver to promoter in the impregnating solution, it is calculated to contain the wt. % of silver, and ppm of promoter indicated.

The following discussion is applicable to all examples.

The analysis for silver is carried out by the following method: An approximately 50 g sample of catalyst is powdered in a mill and 10 g of the powdered sample weighed to the nearest 0.1 mg. The silver in the catalyst sample is dissolved in hot (80° C.), 50% by volume, nitric acid solution. The insoluble alumina particles are filtered and washed with distilled water to remove all adhering nitrate salts of Ag, Cs, etc. This solution is made up to 250 ml in a volumetric flask using distilled water. A 25 ml aliquot of this solution is titrated according to standard procedures using a 0.1 Normal solution of ammonium thiocyanate and ferric nitrate as indicator. The amount of Ag so determined in 250 ml solution is then used to calculate the weight percent silver in the catalyst sample.

Silver and promoter concentrations for all catalysts described in the specification are calculated values as described above.

Carriers are nominally ring shape having dimensions of about ⅜×5/16×5/16 inch or about ¼×¼×¼ inch.

The surface area of the supports is determined by the method of measurement described in "Adsorption Surface Area and Porosity", S. J. Gregg and K. S. W. Sing, *Academic Press* (1967), pages 316–321. The method of measurement for the pore volume is described in ASTM C20-46. The calculated value of the packing density is based on conventional measurement of the weight of the carrier in a known volume container. The method of measurement for the median pore diameter is described in "Application of Mercury Penetration to Materials Analysis", C. Orr, Jr., *Powder Technology*, Vol. 3, pp. 117–123 (1970).

Crush Strength Average and Range is determined according to Test No. 6 as referred to in Catalyst Carriers Norton Company, Akron, Ohio Bulletin CC-11, 1974. Acid Leachable Impurities are determined by contacting carrier pills with 10% nitric acid for one hour at about 90° C. and determining extracted cations by standard Atomic Absorption spectroscopy techniques. Inductively Coupled Plasma Spectroscopy techniques may also be used for such determinations.

The identity and amounts of water leachable components of carriers can be determined by any convenient analytical technique. Generally, the carriers are heated in distilled water at a temperature of about 50° to 95° C., often 90° C., for about 0.5 to 2, e.g., 1 hour. The liquid is then subjected to ion chromatography and Inductively Coupled Plasma Spectroscopy techniques.

Surface acidity is determined by the ammonia chemisorption method. A conventional glass vacuum/adsorption apparatus with a base pressure of $1 \times 10^{-6}$ Torr is used for this purpose. Grease-free stopcocks are used to avoid contamination. Approximately 10 to 15 grams of sample (whole pills or 14/30 mesh) are pretreated in flowing (40 cc/min) helium at 200° C. for 1 hour followed by 15 minutes evacuation at this temperature. Samples are cooled in vacuum to 100° C. for acidity measurements.

The ammonia chemisorption is measured in a static mode by volumetric method of 100° C. Samples are exposed to a known amount of ammonia (15 Torr in a calibrated volume) for period of 45 minutes (or longer until no further ammonia uptake is detected). The ammonia consumption is measured by monitoring its pressure in the system. The ideal gas law is used to calculate the micromoles of absorbed. The sample is then evacuated for 15 minutes at 100° C., and the chemisorption measurement is repeated. The ammonia consumed in this second measurement is subtracted from the first ammonia sorption to provide the amount of ammonia irreversibly (or strongly) sorbed. This measurement is reported in micromoles of ammonia strongly sorbed per gram of sample as a report of sample acidity.

Carrier "A"

Carrier A is an alpha alumina carrier with properties:

| | |
|---|---|
| Surface Area | 1.17 M²/g |
| Water pore volume | 0.65 cc/g |
| Crush strength, FPCS | 7.1 lbs. |
| Total pore volume, Hg | 0.70 cc/g |
| Packing density | 34.2 lbs/ft³ |

| Pore Size Distribution, % Total Pore Volume | |
|---|---|
| Pore Size Microns | % Total Pore Volume |
| P1 (<0.1) | 1.0 |
| P2 (01–0.5) | 10.5 |
| P3 (0.5–1.0) | 11.5 |
| P4 (1.0–10.0) | 22.0 |
| P5 (10.0–100) | 42.0 |
| P6 (|100) | 13.0 |

Acid Leachable Impurities 378 ppm sodium, and 330 ppm potassium

Water Leachable Impurities 9 ppm phosphate, 4 ppm fluoride, 88 ppm aluminum, 2 ppm calcium, 60 ppm potassium, 1 ppm magnesium, 119 ppm sodium, and 157 ppm silicon.

Surface Acidity

The acidity of carrier A is 0.45 micro moles $NH_3$/g carrier.

Carrier "B"

Carrier B is a binderless alpha alumina (99 wt. %) carrier with properties:

| | |
|---|---|
| Surface Area | 1.35 M²/g |
| Water Pore Volume | 0.56 cc/g |
| Packing Density | 61 g/100 ml |
| Median Pore Diameter | 6.3 microns |

| Pore Size Distribution/% Total Pore Volume | |
|---|---|
| Pore Size Microns | % Total Pore Volume |
| P1 (<0.1) | 0.5 |
| P2 (0.1–0.5) | 16.0 |
| P3 (0.5–1.0) | 17.0 |
| P4 (1.0–10.0) | 18.5 |
| P5 (10.0–100) | 38.5 |
| P6 (>100) | 8.5 |

Water Leachable Impurities 168 ppm aluminum, 30 ppm calcium, 1.3 ppm magnesium, 102 ppm potassium, 197 ppm sodium, 148 ppm silicon, 0.8 ppm vanadium, 2.8 ppm phosphorus, 1 ppm chloride, 2 ppm nitrate, 5 ppm phosphate, 1 ppm sulfate, 3 ppm fluoride, 4 ppm acetate, and 1 ppm formate.

Carrier "C"

Carrier is a binderless alpha-alumina carrier. The chemical and physical properties are as follows:

| Chemical Composition of Carrier C | |
|---|---|
| alpha-Alumina | 99 wt. % |
| Water Leachable Impurities: | |
| 40 ppm aluminum, 43 ppm calcium, 1 ppm magnesium, 3 ppm potassium, 27 ppm sodium, 67 ppm silicon, 1.3 ppm phosphorus, 4 ppm chloride, 4 ppm nitrate, 2 ppm phosphate, 1 ppm sulfate. | |
| Physical Properties of Carrier C: | |
| Surface Area | 1.44 m²/g |
| Pore Volume | 0.548 cc/g |
| Packing Density | 62 g/100 ml |

| Pore Size Distribution, % Total Pore Volume | |
|---|---|
| Pore Size Microns | % Total Pore Volume |
| P1 (<0.1) | 1.0 |
| P2 (0.1–0.5) | 20.0 |
| P3 (0.5–1.0) | 16.5 |
| P4 (1.0–10) | 11.5 |
| P5 (10–100) | 41.0 |
| P6 (>100) | 10.0 |

EXAMPLES 1 TO 7

Three stock silver solutions with the following composition are prepared using the general procedure described above to have the following compositions:

| | Stock solution | | |
|---|---|---|---|
| | 1<br>% by wt. | 2<br>% by wt. | 3<br>% by wt. |
| Ethylenediamine | 15.44 | 15.12 | 15.89 |
| Distilled water | 13.77 | 14.18 | 13.9 |
| Oxalic acid dihydrate | 15.47 | 15.23 | 15.92 |
| Silver Oxide | 27.09 | 27.88 | 26.67 |
| Monoethanolamine | 5.42 | 5.58 | 5.93 |

A fluorosulfate standard solution containing 0.02982 gram of cesium and 0.0107 gram of fluorosulfate per gram of solution is also prepared by adding cesium hydroxide and fluorosulfuric acid to distilled water. A cesium sulfate standard solution containing 0.015 gram of cesium per gram of solution is prepared by adding cesium sulfate to distilled water. A cesium molybdate standard solution containing 0.015 gram of cesium per gram of solution is prepared by adding cesium molybdate to distilled water.

The desired amounts of standard solutions are added to a portion of the stock silver solutions to provide the sought impregnating solutions.

The catalysts are prepared by a double impregnation technique as follows. A weighed amount of carrier A is added to an impregnation chamber. The pressure of the chamber is reduced to about 2.0–5.0 mmHg. The impregnation solution is added to the chamber. The pressure of the chamber is brought to atmospheric, and then the excess solution is drained after 20 minutes. The drained solution is retained in a covered beaker. The impregnated carrier is calcined in a belt roaster at about 500° C. for 2.5 minutes as described above. The impregnating and the calcining steps are repeated using the drained solution for the second impregnation.

EXAMPLES 1 AND 2

Stock solution 3 was used to prepare catalysts 1 and 2. The cesium molybdate and the cesium sulfate standard solutions are used to Prepare catalyst 1 and the cesium molybdate and the fluorosulfate standard solutions are used to prepare catalyst 2. Table I summarizes the compositions of the catalysts (promoter concentrations are calculated from solution pick-up):

TABLE I

| Catalyst No. | Ag wt % | Cs ppm | S ppm | F ppm | Mo ppm |
|---|---|---|---|---|---|
| 1 (comparative) | 29.2 | 1598 | 155 | — | 113 |

TABLE I-continued

| Catalyst No. | Ag wt % | Cs ppm | S ppm | F ppm | Mo ppm |
|---|---|---|---|---|---|
| 2 | 30.4 | 1667 | 165 | 98 | 119 |

The catalysts are evaluated in autoclaves as described above using approximately 80 cubic centimeters of catalyst. The feed composition to the autoclave is 30 volume percent ethylene, 8 volume percent oxygen, 6.5 volume percent carbon dioxide, 0.5 volume percent ethane, about 3 ppmv ethylchloride and the balance nitrogen. The total gas flow is 11.3 SCFH. The operating pressure is 275 psig. After starting catalyst, the operating temperature is varied to obtain efficiencies at several outlet ethylene oxide concentrations.

Linear regression analyses are conducted to establish correlations between efficiencies and outlet ethylene oxide concentrations for each catalyst. The resulting equations are given below:

| Catalyst 1: | Eff = 87.02 − % EOout (7.84) |
|---|---|
| Catalyst 2: | Eff = 87.47 − % EOout (4.24) |

The coefficient of the "EOout" term reports the rate of efficiency decrease as EO concentration increases, which reflects the ethylene oxide burning property of the catalyst. As shown in the equations above, the EO burning rate of the fluorine-containing catalyst 2 is lower than that of catalyst 1 which does not contain fluorine but otherwise has the same composition.

EXAMPLES 3 TO 5

Stock solution 1, the cesium sulfate and the cesium molybdate standard solutions are used to prepare catalyst 3. Stock solution 2, the cesium molybdate and the cesium sulfate standard solutions are used to prepare catalyst 4. Stock solution 2, the cesium molybdate and the fluorosulfate standard solutions are used to prepare catalyst 5. The compositions of the catalysts are summarized in Table II below (promoter compositions are calculated from solution pick-up):

TABLE II

| Catalyst No. | Ag wt % | Cs ppm | S ppm | F ppm | Mo ppm |
|---|---|---|---|---|---|
| 3 (comparative) | 31.1 | 934 | 68 | — | 134 |
| 4 (comparative) | 28.9 | 1039 | 75 | — | 150 |
| 5 | 29.5 | 1083 | 93 | 55 | 117 |

The catalysts are evaluated in essentially the same manner as the catalysts in Examples 1 and 2. The efficiency - ethylene oxide concentration correlations obtained for catalysts 3 to 5 are presented below:

| Catalyst 3: | Eff = 85.86 − % EOout (5.36) |
|---|---|
| Catalyst 4: | Eff = 88.10 − % EOout (8.6) |
| Catalyst 5: | Eff = 84.79 − % EOout (3.33) |

Catalyst 5 which contains fluorine has the lowest ethylene oxide burning rate.

EXAMPLES 6 AND 7

Stock solution 3 and the cesium fluorosulfate standard solution are used to prepare catalyst 6. Catalyst 7 is prepared according to the following procedures. About 2183 grams of carrier A are impregnated with a solution prepared using the general procedure described above having the following composition: 1112 grams of ethylene diamine, 1112 grams of oxalic acid dihydrate, 1950 grams of silver oxide, 390.8 grams of monoethanolamine, 6.92 grams of cesium sulfate powder and 2510 grams of distilled water. The impregnated carrier is roasted at 500° C. for 2.5 minutes on a belt roaster with 66.5 SCFH/in² air flow rate as described above. An essentially identical solution to the above except with 8.87 grams of cesium sulfate powder is prepared and used to impregnate the catalyst for a second time with substantially identical procedures to those in the first impregnation.

Table III summarizes the compositions of the catalysts (promoter compositions are calculated from solution pick-up):

TABLE III

| Catalyst No. | Ag wt % | Cs ppm | S ppm | F ppm |
|---|---|---|---|---|
| 6 | 29.8 | 1096 | 135 | 80 |
| 7 (comparative) | 36.2 | 1110 | 134 | — |

The catalysts are evaluated in autoclaves as described previously. The feed composition to the autoclave is 8 volume percent ethylene, 6 volume percent oxygen, 6.5 volume percent carbon dioxide, 0.5 volume percent ethane, about 7.5 ppmv ethylchloride and the balance nitrogen. The total gas flow is 22.6 SCFH. The operating pressure is 275 psig. The efficiency - ethylene oxide concentration correlations for catalysts 6 and 7 and are given below:

| Catalyst 6: | Eff = 85.70 − % EOout (7.48) |
|---|---|
| Catalyst 7: | Eff = 86.99 − % EOout (9.22) |

The catalyst containing fluorine gives a lower ethylene oxide burning rate.

EXAMPLES 8 AND 9

To a 100 ml Pyrex beaker with constant stirring are added:
7.5 grams ethylenediamine,
7.0 ml water,
7.51 grams oxalic acid,
13.16 grams silver oxide, and
2.63 grams monoethanolamine.

The beaker is covered with a watch glass between additions. The temperature of the solution after each addition ranges from 25° C. to 60° C. This mixture is then diluted with distilled water to 35 milliliters.

A cesium perrhenate standard solution containing 0.00531 gram of cesium per gram of solution is prepared by adding an equimolar amount of cesium hydroxide and ammonium perrhenate to distilled water. A fluorosulfate standard solution containing 0.02982 gram of cesium and 0.0107 gram of fluorosulfate per gram of solution is prepared by adding cesium hydroxide and fluorosulfuric acid to distilled water. A cesium sulfate standard solution containing 0.015 gram of cesium per gram of solution is prepared by adding cesium sulfate to distilled water.

The standard solutions are added to the silver oxide-containing solution to provide the sought impregnating solution. The cesium perrhenate solution is heated to 75° C. to assure that the salt is dissolved, and the impregnating solution is warmed to about 40° C. to assure that the cesium perrhenate is dissolved.

Ten grams of support A are added to a Pyrex impregnating chamber. The pressure of the chamber is reduced to about 2.0 to 5.0 mm Hg. The impregnating solution is slowly added to the chamber. The pressure of the chamber is allowed to rise back to atmospheric. The impregnating solution is drained after 20 minutes. The drained solution is retained in a covered beaker. The impregnated support is calcined in a belt roaster as described above at 500° C. for about 3 minutes. The impregnating and calcining steps are repeated using the drained solution for impregnation.

Table IV summarizes the catalysts (the Promoter concentrations are calculated from solution pick-up):

TABLE IV

| Catalyst No. | Ag wt % | Cs ppm | S ppm | F ppm | Re ppm |
|---|---|---|---|---|---|
| 8 (comparative) | 29.5 | 987 | 71 | — | 553 |
| 9 | 29.2 | 995 | 69 | 41 | 557 |

Catalysts 8 and 9 are used in a microreactor to evaluate performance. For the microreactor test, catalyst pills are crushed with a mortar and pestle and screened to the desired size (30-70 mesh). Two grams of crushed catalyst are loaded into a ¼ inch diameter by 5½ inch long stainless steel tube. The tube is placed inside an oven and connected to a gas feed system. The temperature of the oven is controlled by a temperature controller and the reactor outlet pressure is controlled at 150 psig by a Groves back pressure regulator. The gas flow rate is adjusted to the desired gas hourly space velocity (12 liters per hour at standard temperature and pressure). The reaction temperature is measured with two thermocouples inside the reactor. One is immersed in the catalyst bed, about two inches down from the top of the reactor, and the other is located at the reactor outlet. The average of the two readings is recorded as the reaction temperature. The feed composition comprises 30 volume percent ethylene, 8 volume percent oxygen, 6.5 volume percent carbon dioxide, ethane and chlorides as noted in Table V, and nitrogen as the balance of the gas.

alic acid dihydrate is at a rate that the exotherm does not cause the temperature of the solution to rise above 40° C. Then 18.5 grams of silver oxide are added followed by 3.7 grams of monoethanolamine (Fe and Cl free). About 0.62 gram of an aqueous solution containing 0.0222 gram of cesium molybdate per gram solution and 1.63 grams of an aqueous solution containing 0.0577 gram of cesium sulfate per gram solution are added. Distilled water is then added to adjust the solution volume to 40 milliliters. About 20 milliliters of this impregnation solution is used for a first impregnation of carrier B.

Approximately 6.6 grams of carrier B are placed in an impregnation vessel which is evacuated to about 35 mm-Hg absolute at ambient temperature. All the 20 milliliters of the impregnation solution is placed in the impregnation vessel under vacuum and is allowed to contact the carrier for about 3 minutes. The vessel is then opened and the impregnation solution is drained from the carrier.

The catalyst is then roasted in hot air using a belt roaster. The catalyst is spread out in a single layer on a 2 ⅜ inches wide endless stainless steel belt (spiral weave) and transported through a 2 inches by 2 inches square heating zone for 2.5 minutes. Hot air, heated externally by a tubular furnace, is discharged from a 2 inches by 2 inches discharge port immediately below the belt at about 500° C. at a rate of 66 standard cubic feet per hour per square inch.

The remaining 20 milliliters of the impregnation solution are used for a second impregnation. The previously impregnated catalyst is placed in an impregnation vessel which is evacuated to about 35 mm-Hg absolute at ambient temperature. All the 20 milliliters of the impregnation solution are placed in the impregnation vessel under vacuum and allowed to contact the carrier for about 3 minutes. The vessel is then opened and the impregnation solution is drained from the carrier.

The catalyst is then roasted in hot air using a belt roaster. The catalyst is spread out in a single layer on a 2 ⅜ inches wide endless stainless steel belt (spiral weave) and transported through a 2 inches by 2 inches square heating zone for 2.5 minutes. Hot air, heated externally by a tubular furnace, is discharged from a 2 inches by 2

TABLE V

| | Catalyst 8 | | | Catalyst 9 | | | | |
|---|---|---|---|---|---|---|---|---|
| Day | ΔEO % | Efficiency % | Temp °C. | ΔEO % | Efficiency % | Temp °C. | Ethane % | Ethyl chloride ppm |
| 1 | 1.0 | 87.9/86.0[a] | 229 | 1.0 | 87.5 | 235 | 0.72 | 3.6 |
| 2 | — | — | — | 1.2 | 88.2 | 237 | 0.53 | 5.4 |
| 3 | 1.6 | 86.1 | 226 | 1.7 | 86.9 | 242 | 0.53 | 5.4 |
| 4 | 1.9 | 85.6 | 231 | 2.0 | 85.7 | 246 | 0.51 | 7.3 |
| 5 | 2.0 | 85.2 | 235 | 2.1 | 85.2 | 248 | 0.51 | 6.2 |
| 6 | 2.0 | 85.1 | 233 | 2.1 | 84.7 | 247 | 0.51 | 5.4 |
| 7 | 2.1 | 85.3 | 237 | 2.1 | 85.0 | 251 | 0.38 | 7.6 |
| 8 | 2.2 | 84.3 | 237 | 2.3 | 83.0 | 251 | 0.38 | 7.6 |
| 9 | 2.2 | 84.0 | 237 | 2.3 | 82.3 | 251 | 0.38 | 7.6 |
| 10 | 2.3 | 83.0 | 239 | 2.2 | 82.2 | 247 | 0.52 | 7.2 |
| 11 | 2.1 | 83.7 | 235 | 2.0 | 83.6 | 244 | 0.52 | 3.9 |
| 12 | 1.8 | 84.9 | 234 | 1.9 | 84.2 | 244 | 0.52 | 3.8 |

[a]poor mass balance

EXAMPLE 10 (COMPARATIVE)

The preparation technique for catalyst 10 is as follows. An impregnation solution is prepared by mixing 10.6 grams of ethylenediamine (high purity grade) with 8 grams of distilled water. Then 10.6 grams of oxalic acid dihydrate (reagent grade) are slowly added to the mixture at ambient conditions. The addition of the oxinches discharge port immediately below the belt at about 500° C. at a rate of 66 standard cubic feet per hour per square inch.

Catalyst 10 was estimated from solution Pick-up contain 33.6 weight percent silver and 1660 parts per million by weight of cesium.

The performance of catalyst 10 is determined using a 2-inch backmix autoclave. The reactor is a 2-inch stainless steel internal recycle Berty reactor (available from Autoclave Engineers, Inc., Erie, Pennsylvania, U.S.A). The reactor consists of a pressure vessel, a catalyst basket, an impeller, and a Magne-Drive assembly. The pressure vessel has a 2-inch inside diameter and provides the housing for the basket and the impeller. The catalyst basket is a stainless steel cylinder 1.25 inch in diameter and 1.06 inch in length. The bottom of the basket is constructed from a piece of stainless screen which provides a support for catalyst sample and still allows free passage of gas. Six stainless steel strips welded onto the side of the basket serve as baffles that guide the direction of gas flow inside the pressure vessel and as supports for the basket when the basket is inserted into the pressure vessel. The impeller is located above the basket and attached to the inner shaft of the Magne-Drive assembly. An inner shaft housing is attached onto the top of the pressure vessel and forms a closed space with the pressure vessel. The inner shaft is driven through magnetic force by external magnets, which are driven by an air or an electric motor. The rotation of the impeller, normally at 1500 rpm, forces the gas inside the pressure vessel to circulate through the catalyst basket. Reaction gas is fed into the pressure vessel from the top and exits from the bottom. The temperature inside the vessel is controlled and is measured by a thermocouple inserted into the pressure vessel from the bottom.

Approximately 6.4 grams of catalyst 10 are charged to the autoclave. The feed composition is as follows:
oxygen 8 volume percent
ethylene 30 volume percent
ethane 0.5 volume percent
carbon dioxide 6.5 volume percent
ethyl chloride 2 parts per million by volume.

The gas hourly space velocity is 8000 reciprocal hours and the pressure is 275 pounds per square inch gauge. The performance of catalyst 10 is summarized in Table VI.

EXAMPLE 11 (COMPARATIVE)

The preparation technique for catalyst 11 is as follows. An impregnation solution is prepared by mixing 11.1 grams of ethylenediamine (high purity grade) with 8 grams of distilled water. Then 11.1 grams of oxalic acid dihydrate (reagent grade) are slowly added to the mixture at ambient conditions. The addition of the oxalic acid dihydrate is at a rate that the exotherm does not cause the temperature of the solution to rise above 40° C. Then 19.5 grams of silver oxide are added followed by 3.9 grams of monoethanolamine (Fe and Cl free). About 0.65 gram of an aqueous solution containing 0.0222 gram of cesium molybdate per gram solution and 1.29 grams of an aqueous solution containing 0.0577 gram of cesium sulfate per gram solution are added. Distilled water is then added to adjust the solution volume to 40 milliliters. About 20 milliliters of this impregnation solution are used for a first impregnation of carrier B.

Approximately 6.2 grams of carrier B are placed in an impregnation vessel which is evacuated to about 35 mm-Hg absolute at ambient temperature. All the 20 milliliters of the impregnation solution are placed in the impregnation vessel under vacuum and allowed to contact the carrier for about 3 minutes. The vessel is then opened and the impregnation solution was drained from the carrier.

The catalyst is then roasted in hot air using a belt roaster. The catalyst is spread out in a single layer on a 2⅝ inches wide endless stainless steel belt (spiral weave) and transported through a 2 inches by 2 inches square heating zone for 2.5 minutes. Hot air, heated externally by a tubular furnace, is discharged from a 2 inches by 2 inches discharge port immediately below the belt at about 500° C. at a rate of 66 standard cubic feet per hour per square inch.

The remaining 20 milliliters of the impregnation solution are used for a second impregnation. The previously impregnated catalyst is placed in an impregnation vessel which was evacuated to about 35 mm-Hg absolute at ambient temperature. All the 20 milliliters of the impregnation solution are placed in the impregnation vessel under vacuum and allowed to contact the carrier for about 3 minutes. The vessel is then opened an the impregnation solution is drained from the carrier.

The catalyst is then roasted in hot air using a belt roaster. The catalyst is spread out in a single layer on a 2⅝ inches wide endless stainless steel belt (spiral weave) and transported through a 2 inches by 2 inches square heating zone for 2.5 minutes. Hot air, heated externally by a tubular furnace, is discharged from a 2 inches by 2 inches discharge port immediately below the belt at about 500° C. at a rate of 66 standard cubic feet per hour per square inch. Catalyst 11 is estimated from solution pick-up to contain 34.0 weight percent silver and 1290 arts per million by weight of cesium.

The performance of catalyst 11 is determined using a 2-inch backmix autoclave as described above. Approximately 6.4 grams of catalyst 11 are charged to the autoclave. The feed composition is as follows:
oxygen 8 volume percent
ethane 0.5 volume percent
ethyl chloride 2 parts per million by volume
ethylene 30 volume percent
carbon dioxide 6.5 volume percent The gas hourly space velocity is 8000 reciprocal hours and the pressure is 275 pounds per square inch gauge. The performance of catalyst 11 is summarized in Table VI.

EXAMPLE 12

The Preparation technique for catalyst 12 is as follows. An impregnation solution is prepared by mixing 15.9 grams of ethylenediamine (high purity grade) with 12 grams of distilled water. Then 15.9 grams of oxalic acid dihydrate (reagent grade) are slowly added to the mixture at ambient conditions. The addition of the oxalic acid dihydrate is at a rate that the exotherm does not cause the temperature of the solution to rise above 40° C. Then 27.8 grams of silver oxide are added followed by 5.6 grams of monoethanolamine (Fe and Cl free). About 0.94 gram of an aqueous solution containing 0.0221 gram of cesium molybdate per gram solution is added. Distilled water is then added to adjust the solution volume to 60 milliliters. This impregnation solution is used for a first impregnation of carrier B-1.

Carrier B-1 is prepared by soaking carrier B in 10% hydrofluoric acid solution at 25° C. for one hour and then washing with deionized distilled water at 25° C. five times followed by drying in air at 300° C. for 1 hour. The water leachable impurities of carrier B-1 are 266 ppm aluminum, 313 ppm calcium, 5.4 ppm magnesium, 128 ppm Potassium, 106 ppm sodium, 16 ppm silicon, 0.2 ppm vanadium, 0.3 ppm zinc, 1.8 ppm phosphorus, 1 ppm chloride, 10 ppm nitrate, 1 ppm sulfate, and 1011 ppm fluoride.

Approximately 25.7 grams of carrier B-1 are placed in an impregnation vessel which is evacuated to about 35 mm-Hg absolute at ambient temperature. All the 60 milliliters of the impregnation solution are placed in the impregnation vessel under vacuum and allowed to contact the carrier for about 60 minutes. The vessel is then opened and the impregnation solution is drained from the carrier.

The catalyst is then roasted in hot air using a belt roaster. The catalyst is spread out in a single layer on a 2 ⅝ inches wide endless stainless steel belt (spiral weave) and transported through a 2 inches by 2 inches square heating zone for 2.5 minutes. Hot air, heated externally by a tubular furnace, is discharged from a 2 inches by 2 inches discharge Port immediately below the belt at about 500° C. at a rate of 66 standard cubic feet per hour per square inch.

A second impregnation solution is prepared by mixing 15.9 grams of ethylenediamine (high purity grade) with 12 grams of distilled water. Then 15.9 grams of oxalic acid dihydrate (reagent grade) are slowly added to the mixture at ambient conditions. The addition of the oxalic acid dihydrate is at a rate that the exotherm does not cause the temperature of the solution to rise above 40° C. Then 27.8 grams of silver oxide are added followed by 5.6 grams of monoethanolamine (Fe and Cl free). About 0.94 gram of an aqueous solution containing 0.0221 gram of cesium molybdate per gram solution and 0.57 gram of an aqueous solution containing 0.2335 gram of cesium sulfate per gram solution are added. Distilled water is then added to adjust the solution volume to 60 milliliters.

The previously impregnated catalyst is placed in an impregnation vessel which is evacuated to about 35 mm-Hg absolute at ambient temperature. All the second impregnation solution is placed in the impregnation vessel under vacuum and allowed to contact the carrier for about 3 minutes. The vessel is then opened and the impregnation solution is drained from the carrier.

The catalyst is then roasted in hot air using a belt roaster. The catalyst is spread out in a single layer on a 2 ⅝ inches wide endless stainless steel belt (spiral weave) and transported through a 2 inches by 2 inches square heating zone for 2.5 minutes. Hot air, heated externally by a tubular furnace, is discharged from a 2 inches by 2 inches discharge port immediately below the belt at about 500° C. at a rate of 66 standard cubic feet per hour per square inch.

Catalyst 12 is estimated from solution pick-up to contain 33.3 weight percent silver and 930 parts per million by weight of cesium.

The performance of catalyst 12 is determined using a 4 inch backmixed bottom-agitated "Magnedrive" autoclave as described above. Approximately 37 grams of catalyst 12 are charged to the autoclave. The feed composition is as follows:
oxygen 8 volume percent
ethylene 30 volume percent
ethane 0.5 volume percent
carbon dioxide 6.5 volume percent
ethyl chloride 2 parts per million by volume.

The gas hourly space velocity is B000 reciprocal hours and the pressure is 275 pounds per square inch gauge. The performance of catalyst 12 is summarized Table VI.

EXAMPLE 13

The preparation technique for catalyst 13 is as follows. A stock solution is prepared by mixing 2641 grams of ethylenediamine (high purity grade) with 2960 grams of distilled water. Then 2646 grams of oxalic acid dihydrate (reagent grade) are slowly added to the mixture at ambient conditions. The addition of the oxalic acid dihydrate is at a rate that the exotherm does not cause the temperature of the solution to rise above 40° C. Then 4634 grams of silver oxide are added followed by 927 grams of monoethanolamine (Fe and Cl free). A promoter solution is prepared by mixing 200 milliliters of distilled water with 3.08 grams of cesium permanganate and 0.766 gram of cesium molybdate. An impregnation solution was prepared by mixing 4895 grams of the stock solution, 996 grams of distilled water and all the promoter solution. This impregnation solution is used for a first impregnation of carrier C-1.

Carrier C-1 is prepared by soaking carrier C in 10% hydrofluoric acid solution at 25° C. for one hour and then washing with deionized distilled water at 25° C. five times followed by drying in air at 300° C. for 1 hour. The water leachable impurities of carrier C-1 are 606 ppm aluminum, 221 ppm calcium, 7 ppm magnesium, 54 ppm potassium, 66 ppm sodium, 8 ppm silicon, 3 ppm chloride, 5 ppm nitrate, 4 ppm phosphate, 1 ppm sulfate, and 1360 ppm fluoride.

Approximately 2448 grams of carrier C-1 are placed in an impregnation vessel which is evacuated to about 35 mm-Hg absolute at ambient temperature. All the impregnation solution is placed in the impregnation vessel under vacuum and is allowed to contact the carrier for about 30 minutes. The vessel is then opened and the impregnation solution is drained from the carrier.

The catalyst is then roasted in hot air using a belt roaster. The catalyst is spread out in a single layer on a 2 ⅝ inches wide endless stainless steel belt (spiral weave) and transported through a 2 inches by 2 inches square heating zone for 2.5 minutes. Hot air, heated externally by a tubular furnace, is discharged from a 2 inches by 2 inches discharge port immediately below the belt at about 500° C. at a rate of 66 standard cubic feet per hour per square inch.

A second impregnation solution is prepared by mixing 6914 grams of the previously prepared stock solution and 71.95 grams of a second promoter solution. The promoter solution is prepared by adding 3.977 grams of cesium permanganate 0.989 gram of cesium molybdate and 13.445 grams of cesium sulfate to 53.54 grams of distilled water.

The previously impregnated catalyst is placed in an impregnation vessel which is evacuated to about 35 mm-Hg absolute at ambient temperature. All the second impregnation solution is placed in the impregnation vessel under vacuum and is allowed to contact the carrier for about 30 minutes. The vessel is then opened and the impregnation solution is drained from the carrier.

The catalyst is then roasted in hot air using a belt roaster. The catalyst is spread out in a single layer on a 2 ⅝ inches wide endless stainless steel belt (spiral weave) and transported through a 2 inches by 2 inches square heating zone for 2.5 minutes. Hot air, heated externally by a tubular furnace, is discharged from a 2 inches by 2 inches discharge port immediately below the belt at about 500° C. at a rate of 66 standard cubic feet per hour per square inch.

Catalyst 13 is estimated from solution pick-up to contain 30.5 weight percent silver and parts per million by weight of cesium.

The performance of catalyst 13 is determined using a 4-inch backmixed bottom-agitated "Magnedrive" autoclave. Approximately 69 grams of catalyst 13 are charged to the autoclave. The feed composition is as follows:
oxygen 8 volume percent
ethylene 30 volume percent
ethane 0.5 volume percent
carbon dioxide 6.5 volume percent
ethyl chloride 2 parts per million by volume.

The gas hourly space velocity is 8000 reciprocal hours and the pressure is 275 pounds per square inch gauge. The performance of catalyst 13 is summarized in Table VI.

TABLE VI

| Catalyst | Age (day) | Temp. °C. | EO % | Eff. % |
|---|---|---|---|---|
| 10 | 4 | 249 | 0.7 | 77.4 |
|  | 5 | 258 | 1.0 | 74.6 |
| 11 | 2 | 247 | 1.0 | 77.6 |
|  | 3 | 253 | 1.4 | 74.6 |
| 12 | 2 | 234 | 1.4 | 76.8 |
|  | 2 | 246 | 2.0 | 73.8 |
| 13 | 5 | 217 | 1.0 | 81.1 |
|  | 6 | 236 | 2.0 | 79.1 |
|  | 13 | 217 | 1.0 | 82.2 |
|  | 14 | 237 | 2.0 | 79.5 |

EXAMPLE 14

The preparation technique for catalyst 14 is as follows. A stock solution is prepared by mixing 660 grams of ethylenediamine (high purity grade) with 740 grams of distilled water. Then 661 grams of oxalic acid dihydrate (reagent grade) are slowly added to the mixture at ambient conditions. The addition of the oxalic acid dihydrate is at a rate that the exotherm does not cause the temperature of the solution to rise above 40° C. Then 1158 grams of silver oxide are added followed by 232 grams of monoethanolamine (Fe and Cl free). An impregnation solution is prepared by mixing 79 grams of the stock solution, 22 grams of distilled water, 0.0497 gram of cesium permanganate, and 0.558 gram of an aqueous solution containing 0.0221 gram cesium molybdate per gram of solution. This impregnation solution is used for a first impregnation of carrier B-1.

Approximately 33 grams of carrier B-1 are placed in an impregnation vessel which is evacuated to about 35 mm-Hg absolute at ambient temperature. All the impregnation solution is placed in the impregnation vessel under vacuum and is allowed to contact the carrier for about 30 minutes. The vessel is then opened and the impregnation solution is drained from the carrier.

The catalyst is then roasted in hot air using a belt roaster. The catalyst is spread out in a single layer on a 2 ⅜ inches wide endless stainless steel belt (spiral weave) and transported through a 2 inches by 2 inches square heating zone for 2.5 minutes. Hot air, heated externally by a tubular furnace, is discharged from a 2 inches by 2 inches discharge port immediately below the belt at about 500° C. at a rate of 66 standard cubic feet per hour per square inch.

A second impregnation solution is prepared by mixing 112 grams of the previously prepared stock solution, 1.5 grams of distilled water, 0.0625 gram of cesium permanganate, 0.703 gram of an aqueous solution containing 0.0221 gram cesium molybdate per gram of solution, 2.263 grams of an aqueous solution containing 0.0933 gram cesium sulfate per gram of solution.

Approximately 39.4 grams of the previously impregnated catalyst are placed in an impregnation vessel which is evacuated to about 35 mm-Hg absolute at ambient temperature. All the second impregnation solution is placed in the impregnation vessel under vacuum and is allowed to contact the carrier for about 30 minutes. The vessel is then opened and the impregnation solution is drained from the carrier.

The catalyst is then roasted in hot air using a belt roaster. The catalyst is spread out in a single layer on a 2 ⅜ inches wide endless stainless steel belt (spiral weave) and transported through a 2 inches by 2 inches square heating zone for 2.5 minutes. Hot air, heated externally by a tubular furnace, is discharged from a 2 inches by 2 inches discharge port immediately below the belt at about 500° C. at a rate of 66 standard cubic feet per hour square inch.

Catalyst 14 is estimated from solution pick-up to contain 31.3 weight percent silver and 200 parts per million by weight of cesium.

The performance of catalyst 14 is determined using a 4-inch backmixed bottom-agitated "Magnedrive" autoclave. Approximately 33 grams of catalyst 14 are charged to the autoclave. The feed composition is as follows:
oxygen 8 volume percent
ethylene 30 volume percent
ethane 0.5 volume percent
carbon dioxide 6.5 volume percent
ethyl chloride 2 parts per million by volume.

The gas hourly space velocity is 8000 reciprocal hours and the pressure is 275 pounds per square inch gauge. The performance of catalyst 14 is given in Table VII.

EXAMPLE 15 (COMPARATIVE)

The preparation technique for catalyst 15 is as follows. A stock solution is prepared by mixing 660 grams of ethylenediamine (high purity grade) with 740 grams of distilled water. Then 661 grams of oxalic acid dihydrate (reagent grade) are slowly added to the mixture at ambient conditions. The addition of the oxalic acid dihydrate is at a rate that the exotherm does not cause the temperature of the solution to rise above 40° C. Then 1158 grams of silver oxide are added followed by 232 grams of monoethanolamine (Fe and Cl free). An impregnation solution is prepared by mixing 32 grams of the stock solution, 9 grams of distilled water, 0.0199 gram of cesium permanganate, and 0.223 gram of an aqueous solution containing 0.0221 gram cesium molybdate per gram of solution. This impregnation solution is used for a first impregnation of carrier B-2.

Carrier B-2 is prepared by washing carrier B with deionized distilled water at 90° C. five times followed by drying in air at 300° C. for 1 hour. The water leachable impurities of carrier B-2 are 95 ppm aluminum, 49 ppm calcium, 1.8 ppm magnesium, 11 pp potassium, 51 ppm sodium, 110 ppm silicon, 3 ppm chloride, 5 ppm nitrate, and 4 ppm fluoride.

Approximately 21 grams of carrier B-2 are placed in an impregnation vessel which is evacuated to about 35 mm-Hg absolute at ambient temperature. All the impregnation solution is placed in the impregnation vessel under vacuum and is allowed to contact the carrier for about 30 minutes. The vessel is then opened and the impregnation solution is drained from the carrier.

The catalyst is then roasted in hot air using a belt roaster. The catalyst is spread out in a single layer on a 2 ⅜ inches wide endless stainless steel belt (spiral weave) and transported through a 2 inches by 2 inches square heating zone for 2.5 minutes. Hot air, heated externally by a tubular furnace, is discharged from a 2 inches by 2 inches discharge port immediately below the belt at about 500° C. at a rate of 66 standard cubic feet per hour per square inch.

A second impregnation solution is prepared by mixing 42 grams of the previously prepared stock solution, 2 grams of distilled water, 0.025 gram of cesium permanganate, 0.28 gram of an aqueous solution containing 0.0221 gram cesium molybdate per gram of solution, 0.903 gram of an aqueous solution containing 0.0933 gram cesium sulfate per gram of solution.

Approximately 12.7 grams of the previously impregnated catalyst are placed in an impregnation vessel which is evacuated to about 35 mm-Hg absolute at ambient temperature. All the second impregnation solution is placed in the impregnation vessel under vacuum and is allowed to contact the carrier for about 30 minutes. The vessel is then opened and the impregnation solution is drained from the carrier.

The catalyst is then roasted in hot air using a belt roaster. The catalyst is spread out in a single layer on a 2 ⅜ inches wide endless stainless steel belt (spiral weave) and transported through a 2 inches by 2 inches square heating zone for 2.5 minutes. Hot air, heated externally by a tubular furnace, is discharged from a 2 inches by 2 inches discharge port immediately below the belt at about 500° C. at a rate of 66 standard cubic feet per hour per square inch.

Catalyst 15 is estimated from solution pick-up to contain 30.9 weight percent silver and 1200 parts per million by weight of cesium.

The performance of catalyst 15 is determined using a 2-inch backmixed autoclave. Approximately 5.5 grams of catalyst 15 are charged to the autoclave. The feed composition was as follows:
oxygen 8 volume percent
ethylene 30 volume percent
ethane 0.5 volume percent
carbon dioxide 6.5 volume percent
ethyl chloride 2 parts per million by volume.

The gas hourly space velocity is 8000 reciprocal hours and the pressure is 275 pounds per square inch gauge. The performance of catalyst 15 is summarized in Table VII.

TABLE VII

| Catalyst | Age (day) | Temp. °C. | EO % | Eff. % |
|---|---|---|---|---|
| 14 | 2 | 224 | 1.0 | 80.9 |
|  | 3 | 240 | 2.0 | 78.5 |
| 15 | 2 | 231 | 1.0 | 78.0 |
|  | 3 | 243 | 2.0 | 74.5 |

It is claimed:

1. A catalyst for the epoxidation of ethylene to the ethylene oxide comprising a catalytically effective amount of silver impregnated on an inert, refractory solid support which support has an essential absence of fluoride anion, said catalyst further containing an efficiency enhancing amount, relative to the amount of silver metal, of promoter comprising cation selected from at least one member of the group of lithium, sodium, potassium, rubidium, cesium, and barium and anion comprising (i) sulfate, (ii) fluoride and (iii) at least one member of the group of oxyanions of elements having atomic numbers of 21 to 74, inclusive, selected from Groups 3b to 6b, inclusive, of the Periodic Table of Elements, wherein the sulfate and fluoride anions may be in the form of fluorosulfate and the fluoride anion is also in an amount sufficient to reduce ethylene oxide burning as compared to an otherwise identical catalyst but not containing the fluoride anion and its associated cation.

2. The catalyst of claim 1 in which the at least one oxyanion of elements having atomic numbers of 21 to 74, inclusive, is selected from Group 5b and 6b of the Periodic Table of the Elements.

3. The catalyst of claim 2 in which the at least one oxyanion of elements having atomic numbers of 21 to 74, inclusive, is oxyanion of molybdenum.

4. The catalyst of claim 1 in which the cation promoter comprises cesium cation.

5. The catalyst of claim 4 in which the at least one oxyanion of elements having atomic numbers of 21 to 74, inclusive, is selected from Group 5b and 6b of the Periodic Table of the Elements.

6. The catalyst of claim 5 in which the at least one oxyanion of elements having atomic numbers of 21 to 74, inclusive, is oxyanion of molybdenum.

7. The catalyst of claim 1 in which the atomic ratio of Group 3b to 6b element of the oxyanion to sulfur is between about 1:10 to 10:1.

8. The catalyst of claim 7 in which the atomic ratio of sulfur to fluorine is between about 1:10 to 10:1.

9. The catalyst of claim 8 in which the at least one oxyanion of elements having atomic numbers of 21 to 74, inclusive, is selected from Group 5b and 6b of the Periodic Table of the Elements.

10. The catalyst of claim 9 in which the at least one oxyanion of elements having atomic numbers of 21 to 74, inclusive, is oxyanion of molybdenum.

11. The catalyst of claim 2 in which the total anion promoter is provided from about 0.001 to 0.5 weight percent based on the total weight of the catalyst.

12. The catalyst of claim 11 in which the cation promoter is provided in an amount of 10 to 2000 ppmw.

13. The catalyst of claim 12 in which fluoride anion is present in an amount of at least 20 ppmw.

14. The catalyst of claim 13 in which the atomic ratio of sulfur to fluorine is between about 1:10 to 10:1

15. The catalyst of claim 14 in which the support is alpha-alumina.

16. The catalyst of claim 2 in which the support is alpha-alumina.

17. The catalyst of claim 1 in which the at least one oxyanion of elements having atomic numbers of 21 to 74, inclusive, is oxyanion of tungsten.

* * * * *

UNITED STATES PATENT AND TRADEMARK OFFICE
CERTIFICATE OF CORRECTION

PATENT NO. : 5,102,848

DATED : April 7, 1992

INVENTOR(S) : H. Soo et al

It is certified that error appears in the above-indentified patent and that said Letters Patent is hereby corrected as shown below:

Column 26, line 31, "arts" should read "parts".

Column 27, line 65, "B000" should read "8000".

Signed and Sealed this

Twenty-eighth Day of September, 1993

*Attest:*

BRUCE LEHMAN

*Attesting Officer*  *Commissioner of Patents and Trademarks*